United States Patent [19]

Prodi

[11] Patent Number: 4,639,311
[45] Date of Patent: Jan. 27, 1987

[54] DEVICE FOR SEPARATING AIRBORNE PARTICLES INTO GRAIN SIZE CLASSES

[76] Inventor: Vittorio Prodi, Via Martinelli, 7, 40137 Bologna, Italy

[21] Appl. No.: 723,670

[22] Filed: Apr. 16, 1985

[30] Foreign Application Priority Data

Apr. 19, 1984 [IT] Italy ................................ 3433 A/84

[51] Int. Cl.$^4$ ................................................ B07B 7/086

[52] U.S. Cl. .................................... 209/143; 209/144; 55/261; 55/434; 55/439 DIG. 14

[58] Field of Search ............... 209/143, 210, 154, 144; 55/261, 461, 434, 439, DIG. 14

[56] References Cited

U.S. PATENT DOCUMENTS

| | | | |
|---|---|---|---|
| 3,865,242 | 2/1975 | Musto | 209/143 |
| 4,111,671 | 9/1978 | Williamson | 55/461 |
| 4,153,541 | 5/1979 | Rumpf et al. | 209/143 |
| 4,159,942 | 7/1979 | Greer et al. | 209/143 |

*Primary Examiner*—Kenneth M. Schor
*Assistant Examiner*—Thomas M. Lithgow
*Attorney, Agent, or Firm*—Omri M. Behr

[57] ABSTRACT

A device is described for separating airborne particles into grain size classes.

The principle characteristic of the present invention lies in the fact that it comprises:

a first base body formed as a cup in which there are formed three chambers which are upwardly open and in each of which there is created in use a depression with a respective predetermined value;

a first channel formed in a second upper body, of substantially L-shape form and having a first cavity into which filtered air flows in use, and a second cavity facing the entrance of the said chamber communicating by means of a sharp curvature with the said first cavity; and a nozzle positioned in the said first cavity and operable to inject into it a quantity of particle-bearing air in such a way that the particles of dust present in this are sub-divided into various grain size classes in dependence on the aerodynamic diameter thereof, to flow into the said chamber in quantities which are a function of the difference of the various values of the pressure existing in these.

13 Claims, 1 Drawing Figure

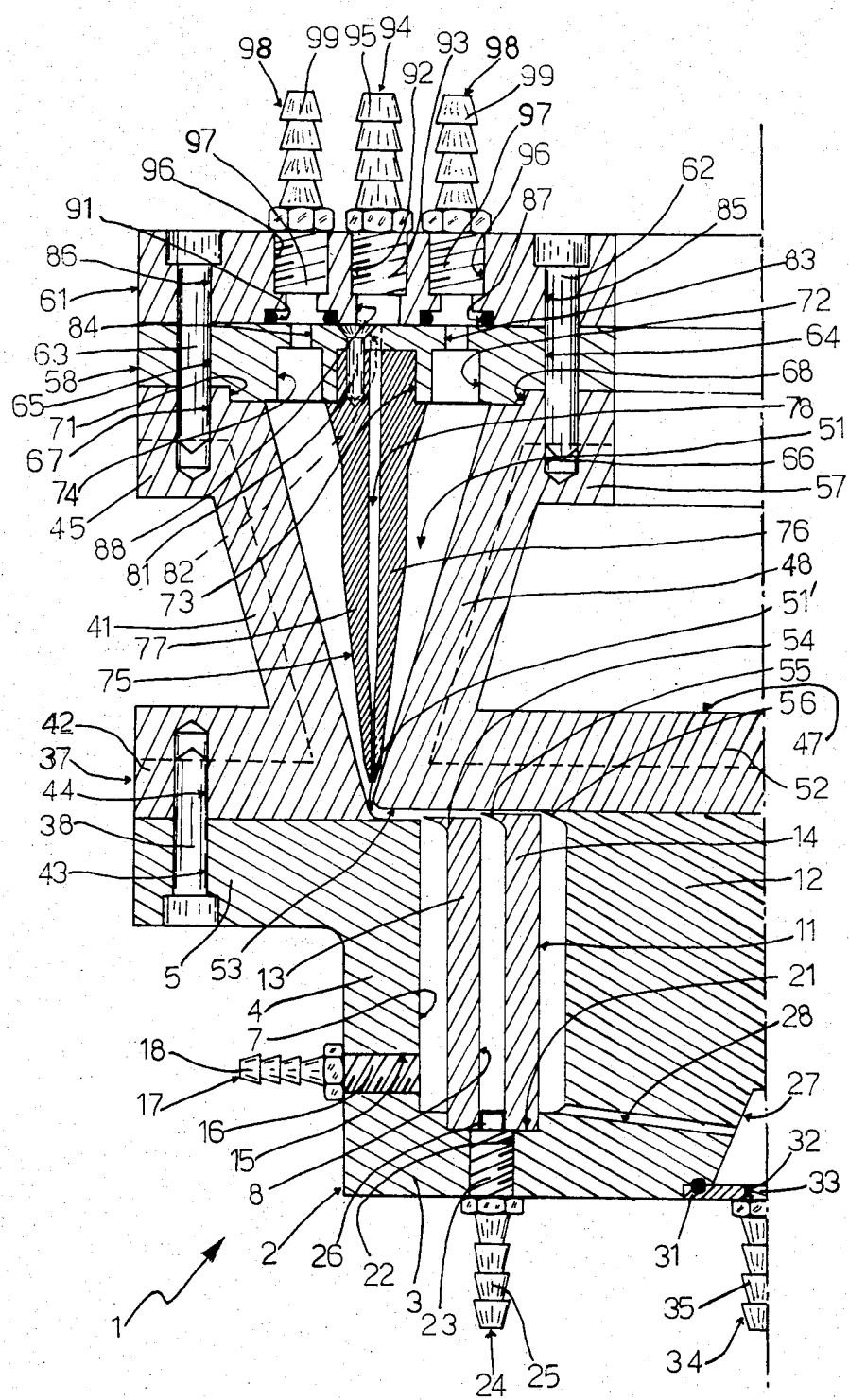

DEVICE FOR SEPARATING AIRBORNE PARTICLES INTO GRAIN SIZE CLASSES

BACKGROUND OF THE INVENTION

The present invention relates to a device for separating airborne particles, such as particles of an aerosol, into classes by grain size.

The devices which are currently available have been conceived to measure the distribution of the particles. In fact, these are instruments which separate the particles still in suspension in air (aerosol) and which collect them on a filter maintaining the separation. Upon deposition it is then possible to perform all the analyses required from time to time for industrial and environmental health, medical physics, and powder technology generally, to obtain grain size separation of the aerosol. Such devices generally comprise a channel of rectangular section and of L-shape form through which filtered air passes; the particle-bearing air is injected into the first part of the channel upstream of the curvature which separates the first part from the second; upon passing the sharp curvature of the channel the particles tend by inertia to maintain their velocity in sense and direction, but are carried along by the flow. The particles having the same dimension become disposed in the same streamline which comes into contact with a well defined region of the filter; therefore such particles are separated from the initial flow of fluid by a distance which is a function only of aerodynamic diameter and the filter collects the particles which are arranged in different positions according to their aerodynamic dimensions.

SUMMARY OF THE INVENTION

The object of the present invention is to provide a device of the first indicated type which can separate airborne particles, particularly particles of an aerosol, into grain size classes, which allows the particles of one grain size class to be isolated from the others to obtain the greatest amount of information therefrom, whilst maintaining them in suspension.

Further objects and advantages of the present invention will become apparent from the following description.

According to the present invention there is provided a device for separating airborne particles into grain size classes, characterised by the fact that it comprises:

a first base body of upwardly open cup-shape form in which are formed, in succession, a first, second and a third chamber also upwardly open and in which there is created, in use, a depression with a respective predetermined value;

a first channel formed in a second upper body with a substantially L-shape conformation having a first cavity into which, in use, filtered air flows and a second cavity facing the entrance of the said first, second and third chambers and communicating via a sharp curvature with the said first cavity; and a nozzle positioned in the said first cavity and operable to inject into it, close to the said curvature, a quantity of particle-bearing air in such a way that the particles of dust present therein after having traversed the said curvature separate into various grain size classes in dependence on their diameter to flow into the said first, second and third chambers in quantities depending on the various pressure values existing therein.

DETAILED DESCRIPTION OF THE INVENTION

For a better understanding of the present invention a preferred embodiment will now be described, purely by way of non limitative example, with reference to the attached drawing in which there is illustrated a partial section of a device operable to separate air-borne particles into grain size classes, and generally indicated with the reference numeral 1. The device 1 comprises a base body 2 of cup-shape form having a cylindrical base wall 3 from the lateral edge of which extends upwardly a lateral wall 4 of cylindrical shape. From the upper end of this lateral wall 4 extend outwardly, parallel to the said base wall 3, an annular projection 5. Within the body 2 there are formed three concentric annular chambers, respectively indicated 7,8 and 11. From the central zone of the upper surface of the base wall 3 extends, upwardly, a cylindrical element 12; from the upper surface of the base 3, moreover there extends upwardly two annular elements 13 and 14 concentric with the element 12 and of which that indicated 14 lies within the other. The chamber 7, which is the outermost, is delimited by the inner surface of the lateral wall 4 and by the outer surface of the element 13, the chamber 8 is delimited by the inner surface of the element 13 and the outer surface of the element 14, and the chamber 11, which is the innermost, is delimited by the inner surface of the element 14 and by the outer surface of the element 12.

In use a vacuum is created in the chambers 7,8 and 11, with different values in each chamber. For this, each chamber 7,8 and 11 communicate with a respective pump operating to create this depression. On the side wall 4 there is formed a threaded radial through hole 15 into which is screwed a threaded portion 16 of a first pipe union 17 an outer portion 18 of which projects radially from the hole 15 to support the end of a duct, not illustrated, operable to put a first pump into communication with the chamber 7. On the upper surface of the base wall 3 there is formed an annular groove 21 which houses the lower ends of the elements 13 and 14. In the groove 21 in the wall 3 there is formed a threaded through hole 22 engaged by a threaded upper portion 23 of a second pipe union 24 a lower portion 25 of which projects downwardly from the hole 22 to support the end of a duct, not illustrated, operable to put a second pump into communication with the chamber 8. From the portion 23 a projection 26 extends, towards the interior of the groove 21, acting to maintain the elements 13 and 14 spaced from one another. In correspondence with the central zone of the lower surface of the base wall 3 there is formed a cavity 27 communicating with the chamber 11 by means of a passage 28. Around the lateral edge of the cavity 27 there is fixed a small plate 31 having a central threaded through hole 32 engaged by an upper portion 33 of a third pipe union 34 a lower portion 35 of which extends downwardly and supports the end of a duct, not illustrated, operable to put a third pump into communication with the chamber 11.

As illustrated in the attached drawing the device 1 includes an annular body 37 coaxial with the body 2 and fixed to this by screws 38. The body 37 has a central portion 41 of substantially frusto-conical form and of constant thickness, with the upper end being of greater diameter. From the lower end of the portion 41 an annular projection 42 extends outwardly and its lower surface faces the upper surface of the projection 5 of the body 2. The projection 5 has a plurality of through holes 43 coaxial with a corresponding number of blind threaded holes 44 formed in the projections 42. The screws 38 first engage the holes 43 and subsequently are screwed into the holes 44. From the upper end of the portion 41 a second annular projection 45 extends outwardly parallel to the projection 42.

The device 1 further includes an annular body 47 coaxial with the body 37 and inside this latter. The body 47 has a central portion 48 of substantially frusto-conical form and of constant thickness, with its smaller diameter end uppermost. The inner surface of the portion 41 of the body 37 and the outer surface of the portion 48 of the body 37 define an annular channel 51 having a decreasing width from the top towards the bottom. The lower end of the portion 48 is fixed to the perimetral edge of a cylindrical plate 52 parallel to the base wall 3 of the body 2 and the lower surface of which rests on the upper wall of the cylindrical element 12. This latter extends beyond the upper end of the lateral wall 4 of the body 2 and therefore the plate 52 resting on the element 12 defines an annular cavity 53 between its lower surface and the upper end of the wall 4. It is to be noted that the annular element 13 extends beyond the upper end of the wall 4 and that the annular element 14 extends beyond the upper end of the element 13; the upper ends of the elements 13 and 14 are therefore separated by different distances from the lower surface of the plate 52. The elements 13,14 and 12 have an upper end from which extends, outwardly, a respective annular projection 54,55 and 56 which is tapered with a decreasing thickness and the upper face of which is coplanar with the upper face of the respective elements 13,14 and 12. The outer ends of the projections 54,55 and 56 define with the corners of the upper ends, respectively, of the wall 4, the element 13 and the element 14, the mouths of the chambers 7,8 and 11 which can put these into communication with the cavity 53. It is to be noted further that the cavity 53 communicates with the channel 51 by the fact that the lower ends of the portions 41 and 48 are of different diameter and therefore define an annular outlet mouth indicated 51' and hereinafter called for simplicity an outlet; the corners of such ends are rounded to render the passage from the channel 51 to the channel 53 gradual. From the upper end of the portion 48 an annular projection 57 extends inwardly coplanar with the projection 45.

The device 1 includes two annular plates 58 and 61 coaxial with one another and with the bodies 37 and 47. In particular the inner rims of the plates 58 and 61 are fixed by screws 62 to the projection 57 of the body 47 and the outer rims of these are fixed by screws 63 to the projection 45 of the body 37. The plate 58 rests directly on the upper surface of the projections 45 and 57 and in this respect has an inner ring of through holes 64 and an outer ring of through holes 65. The holes 64 are co-axial with a corresponding number of blind threaded holes 66 formed in the projection 57 and the holes 65 are co-axial with corresponding holes 67 formed in the projection 45. A central ring of the plate 58 has a greater thickness than the inner and outer rims. The inner and outer edges of this central ring rest, respectively, on an annular recess 68 formed at the upper end of the portion 48 and on an annular recess 71 formed at the upper end of the portion 41. The lower surface of the central ring of the plate 58 faces the channel 51 and has three annular grooves respectively indicated 72, 73 and 74. The grooves 72 and 74 are respectively the innermost and outermost and have the same width. The groove 73, which is the central groove, has a greater width than the others and houses the upper end of a nozzle 75 constituted by two annular bodies 76 and 77 co-axial with one another and with the bodies 37 and 47; the body 76 is within the body 77 and defines with this an annular channel 78. The bodies 76 and 77 are fixed to the plate 58 at their upper ends by means of a plurality of screws 81 only one of which is illustrated for simplicity and is shown fixing the body 77 to the plate 56. Along the groove 73 in the plate 58 there is formed a plurality of through holes 82 (one of which is illustrated in broken outline in the attached drawing) which open into the channel 78. Along the grooves 72 and 74 in the plate 58 there is formed a respective plurality of through holes 83 and 84.

The plate 61 rests on the plate 58 and has a ring of through holes 85 coaxial with the holes 64 and a ring of through holes 86 coaxial with the holes 65. Each screw 62 engages in succession a hole 85 and a hole 64 and is screwed into the hole 66. Each screw 63 engages in succession into a hole 86 and a hole 65 and is screwed into a hole 67. The central ring of the plate 61, which, corresponds to the central ring of the plate 58, has on its lower surface three annular grooves 87, 88 and 91 the groove 87 of which is in communication with the holes 83, the groove 88 of which is in communication with the holes 82, and the groove 91 of which is in communication with the holes 84. Along the groove 88 in the plate 61 there are formed threaded holes 92 into which there is screwed a lower threaded portion 93 of a respective pipe union 94 having an upper portion 95 extending upwardly and supporting the end of a duct, not illustrated, which via the groove 88 and the holes 82, puts the channel 78 into communication with a source of aerosol which could be the environment itself. Along the grooves 87 and 91 are formed respective threaded holes 96 into which are screwed the lower portions 97 of respective pipe unions 98 each having an upper portion 99 extending upwardly. The pipe unions 98 are connected to a source of filtered air via respective ducts not illustrated, which air is conveyed into the channel 51 via the grooves 72 and 74.

The technique for the separation of aerosol particles into grain size classes is known and is described in various scientific publications. It consists in the fact that, as already indicated, the particles flowing past a sharp curvature (outlet 51') tend by inertia to maintain their velocity in direction and sense, and therefore downstream of the curvature itself are separated into various bands of fluid according to their aerodynamic diameter. For the correct operation of the device 1, that is for a better separation of the particles into various grain size classes, the longitudinal axis of a representative section of the nozzle 75 is offset towards the outer surface of the portion 48. This characteristic has been shown experimentally to be valid and is described in the said publications.

The operation of the device 1 is as follows.

In detail, filtered air from a suitable source is introduced into the channel 51 and a quantity of aerosol from a second source, which could be the environment itself, is injected via the nozzle 75 into the channel 51 close to the outlet 51'. This is possible, for example, by creating a depression in the chambers 7, 8 and 11 which draws in the filtered air and the aerosol. The fluid constituted by filtered air and aerosol flows past the sharp curvature (51') where the particles of dust present in the aerosol separate out from one another in dependence on their aerodynamic diameter into various bands of fluid, that is all the particles of the same grain size class will be present within their streamline. If a filter had been positioned in place of the elements 13, 14 and 12 the particles would be deposited on this starting from the particles of greater diameter. Since there is no filter there, it will happen in the device 1, that the depression in the chambers 7, 8 and 11 being equal, the particles which belong to the grain size classes of greater diameter will flow into the chamber 7 whilst the particles of medium diameter will flow into the chamber 8 and the particles of smallest diameter will flow into the chamber 11. By playing with the values of the depression in the chambers 7, 8 and 11 it is possible to isolate the particles of the classes which flow, for example, into the chamber 8. In fact, if there is created in the chamber 8 a pressure having an absolute value of less than that of the chamber 7 the particles of some grain size classes with greater diameter particles will flow into the chamber 8; in other words by varying the depression within the chambers 7, 8 and 11, particles belonging to grain size classes which range from those of larger diameter to those of smaller diameter will be brought together in the chamber 8, which is that which is of greatest interest here. With the device 1 it is possible therefore to isolate particles of a single class or several classes, thus obtaining particles of homogeneous diameter. If a device similar to the device of the invention but having a filter inserted is put in cascade with it, particles belonging to the predetermined class or classes are deposited on the filter and therefore isolated by this from the others; with deposition thus obtained it is then possible to effect all the analyses necessary for the determination of the characteristics of such particles. It is natural that the particles of the isolated classes will be deposited on the filter according to sub-classes and therefore from the deposition it is possible to have all the information on the characteristics of such classes.

In the chambers 7, 8 and 11, it is possible to take an optical reading for the determination in real time of the quantity of particles which traverse the chambers 7, 8 and 11. For such optical reading a photometer can be used, for example of the laser beam type to be housed in a suitable recess formed in one of the surfaces which delimit the chamber of interest.

From what has been explained above the advantages which flow from the present invention will be apparent.

In particular, with the device of the invention it is possible to isolate particles of one or more grain size classes from the others without deposition. It is therefore possible to utilise such device as a source of particles of a particular grain size class; if the device itself is put in cascade with a similar device having a filter it is possible to collect information relating to the class which is deposited on the filter in sub classes. It is also apparent, therefore, that by utilising the device as a source of particles it is possible to calibrate filter devices for a correct determination of the calibration curve of these latter.

Finally, it is clear that the device described and illustrated here can be modified and varied without by this departing from the scope of protecting of the present invention.

In particular, the geometry of the bodies 2, 37 and 47 and the nozzle 75 can be different from that described whilst remaining within the principal of providing the body 2 with several chambers, for example, 3 chambers even non-annular ones, but in which a different value of depression is created. For example the channel 51 and the nozzle 75 could have a pyramid geometry as provided in devices currently in commercial use; analogously the interior of the body 2 could be of prismatic geometry and the elements 13 14 and 12 transformed into normal flat dividing walls. It is also important to note that the device can utilise the upper part (bodies 37 and 47) of a device of the same type but provided with a filter by coupling this latter to a lower part (body 2) in which the chambers 7, 8 and 11 are formed.

I claim:

1. A device employing a source of filtered air and means to create a negative pressure for separating from a source of suspensoids airborne particles, such as an aerosol, into a plurality of suspensoids of airborne particles each containing particles of predetermined grain size classes, comprising:

a first body including a base wall having extending transversely therefrom a side wall, a first and second dividing wall and a third wall, said side wall and said first dividing wall defining between them a first chamber, a second chamber being defined between said first and second dividing wall, said second dividing wall and said third wall defining a third chamber, said base wall having an outlet opening communicating with each of said first, second, and third chambers and outlet means adapted to separately connect said means to create a negative pressure to at least one of said first, second and third chamber outlets;

a second upper body defining a first cavity having an inlet opening communicating with said source of filtered air, the connection of said second body to said first body defining a second cavity and an elbow passage way at one end of said second cavity providing a communication between said first and second cavities, said first, second, and third chambers being open to and communicating with said second cavity at the other end thereof; and a nozzle positioned in said first cavity in said first cavity and adapted to be connected to said source of suspensoids and operable to eject said suspensoides through said elbow passageway, said nozzle being positioned and said elbow joint being curved in such a way that the suspensoids after having traversed said elbow passageway separate into a plurality of grain size classes each flowing into a predetermined one of said first, second and third chambers in dependence on the magnitude of negative pressure formed therein.

2. The device according to claim 1, characterised by the fact that the upper end of the first said dividing wall is higher than the upper end of the said side wall, the upper end of the said second dividing wall is higher than the first dividing wall, and the upper end of the said third wall is higher than the second dividing wall, the lower surface of a base plate of the said second body resting on the upper end of the said third wall and defining, with the upper end of the said side wall, the said second cavity.

3. A device according to claim 2, characterised by the fact that a respective tapered projection extends towards the said side wall from the upper end of the said first and second dividing walls and the said third wall in such a way as to delimit and facilitate the ingress of said plurality of separated grain classes into the respective said first, second, and third chambers.

4. A device according to claim 3, characterised by the fact that the said first body has a cylindrical geometry and the said base wall has a circular outline and the said side wall has a cylindrical form; the said first dividing wall of cylindrical form, the said second dividing wall inside and concentric to this latter, and also of cylindrical form, and the said third inner wall concentric to this latter and constituted by a cylindrical element, all extending upwardly from the upper surface of the said base wall in such a way that the said first, second and third chambers are of annular form.

5. A device according to claim 4, wherein said outlet means comprises a first pipe union able to put the said first chamber in communication with a first means to create a negative pressure therein, a second pipe union able to put the said second chamber into communication with a second means to create a negative pressure therein, and a third pipe union able to put the said third chamber into communication with a third means to create a negative pressure therein.

6. A device according to claim 4, characterised by the fact that the said second body comprises:
a first annular element fixed to the said first body in correspondence with the upper face of the said side wall and having a central portion describing with its inner surface the lateral surface of a frusto-conical solid with the larger diameter section positioned higher than the lower diameter section; and
a second annular element within the said first annular element and comprising a base plate with a central portion extending upwardly from the lateral edge of the said base plate and describing with its outer surface the lateral surface of a frusto-conical solid with the larger diameter section positioned lowermost in such a way as to define, with the inner surface of the said central portion of the said first annular element, the said first cavity which thus has an annular form and communicates with the said second cavity via the said elbow passageway formed by suitably joining the lower ends of the said lateral portions respectively of the said first and second annular elements; the said nozzle also being of annular form.

7. A device according to claim 6, characterised by the fact that the said nozzle includes two, third annular elements one within the other and defining between them a second channel communication with a source of suspensoids.

8. A device according to claim 7, characterised by the fact that the said nozzle is disposed in the said first cavity in such a way as to be close to the said central portion of the said second annular element.

9. A device according to claim 7, characterised by the fact that the said third annular elements are supported by a first plate positioned above the said first and second annular elements and fixed to these in such a way that the said first annular element supports the said second annular element via the said first plate.

10. A device according to claim 9, characterised by the fact that it includes a second plate positioned above the said first plate and in which is formed a fourth hole engaged by a portion of a fourth pipe union connected to the source of suspensoids; the said fourth hole being in communication with the said second channel via a plurality of fifth holes formed in the said first plate.

11. A device according to claim 10, characterised by the fact that at least one sixth hole is formed in the said second plate and engaged by a portion of a fifth pipe union connected to the source of filtered air; the said sixth hole being in communication with the said first cavity via a plurality of seventh holes formed in the said first plate.

12. A device according to claim 11, characterised by the fact that the said first plate has on its lower surface facing the said first cavity a first groove in which are fixed the upper ends of the said third annular elements; the said fifth holes being formed in the said first groove and communicating below with the said second channel and above, via a second annular groove formed on the lower surface of the said second plate, with the said fourth hole formed in the said second groove.

13. A device according to claim 12, characterised by the fact that the said first plate has, on its lower surface facing the said first cavity, at least one, third annular groove concentric with the said first groove and open towards the said first cavity; the said seventh holes being formed in the said third groove and communicating above, via a fourth annular groove formed in the lower surface of the said second plate concentrically with the said second groove, with the said sixth hole formed in the said fourth groove.

* * * * *